United States Patent
MacKenzie

(12) 
(10) Patent No.: US 6,252,928 B1
(45) Date of Patent: Jun. 26, 2001

(54) METHOD AND DEVICE FOR ESTIMATING BONE MINERAL CONTENT OF THE CALCANEUS

(75) Inventor: Innes K. MacKenzie, Guelph (CA)

(73) Assignee: Guard Inc., Guelph (CA)

( * ) Notice: Subject to any disclaimer, the term of this patent is extended or adjusted under 35 U.S.C. 154(b) by 0 days.

(21) Appl. No.: 09/235,236

(22) Filed: Jan. 22, 1999

Related U.S. Application Data

(60) Provisional application No. 60/072,312, filed on Jan. 23, 1998.

(51) Int. Cl.$^7$ .................................................. G01B 15/02
(52) U.S. Cl. ................................................ 378/54; 378/89
(58) Field of Search .................................. 378/54, 86, 88, 378/89, 207

(56) References Cited

U.S. PATENT DOCUMENTS

| | | | |
|---|---|---|---|
| 4,320,749 | * | 3/1982 | Highley ................................. 378/208 |
| 4,721,112 | | 1/1988 | Hirano et al. . |
| 4,829,549 | | 5/1989 | Vogel et al. . |
| 4,903,203 | | 2/1990 | Yamashita et al. . |
| 5,204,888 | | 4/1993 | Tamegai et al. . |
| 5,335,260 | | 8/1994 | Arnold . |
| 5,351,689 | | 10/1994 | MacKenzie . |
| 5,509,042 | | 4/1996 | Mazess . |
| 5,521,955 | | 5/1996 | Gohno et al. . |
| 5,910,972 | * | 6/1999 | Ohkubo et al. ........................ 378/54 |

OTHER PUBLICATIONS

Methods of Bone Mineral Measurement, Tothill, P., Physics in Medicine and Biology, 1989, vol. 43, No. 5, 543–572.*

* cited by examiner

Primary Examiner—David P. Porta
(74) Attorney, Agent, or Firm—Lynn C. Schumacher; Hill & Schumacher

(57) ABSTRACT

The present invention provides an in situ, low dose and noninvasive method and device for estimating bone mineral content of trabecular bones, particularly the calcaneus. The method of estimating bone mineral content involves measuring the intensity of X-rays backscattered from the calcaneus and estimating the calcium content from this intensity. The apparatus includes an axially symmetric heavy-metal radioactive source holder (collimator) containing a radioactive source mounted on the axis of a cylindrically symmetric scintillation counter or detector. In a preferred embodiment of the device, a $^{109}$Cd radioactive source that emits the K X-rays of silver (22 to 25 Kev) is used. A person's foot is immobilized on the apparatus with a spring-loaded X-ray collimator bearing against the back of the heel. The method relies upon measuring the total intensity of X-rays backscattered from the calcaneus (heel bone). The X-ray energy is selected on the basis that it is low enough to ensure a strong contrast in the absorption of both the primary and scattered X-rays because of the presence of calcium. X-rays are backscattered primarily via Compton scattering and are detected by the scintillation detector. Periodic measurements of the calcium content in a person's caleaneus using the present method and device permits one to monitor the development of osteoporosis based on changes in the X-ray albedo of the calcaneus resulting from changes in concentration of calcium phosphate over time.

22 Claims, 2 Drawing Sheets

METHOD AND DEVICE FOR ESTIMATING BONE MINERAL CONTENT OF THE CALCANEUS

CROSS REFERENCE TO RELATED U.S. PATENT APPLICATION

This patent application relates to U.S. Provisional patent application Ser. No. 60/072,312 filed on Jan. 23, 1998 entitled METHOD AND DEVICE FOR ESTIMATING BONE MINERAL CONTENT OF THE CALCANEUS.

FIELD OF THE INVENTION

The present invention relates in general to a low dose, in situ and noninvasive method and device for estimating human bone mineral content and more particularly the present invention relates to a method for monitoring osteoporosis by using the X-ray albedo as a measure of the calcium content of the calcaneus.

BACKGROUND OF THE INVENTION

Osteoporosis is a condition of the human skeleton that is characterized by deleterious loss, over time, of bone mineral content, particularly calcium. The disease, while most prevalent in women past menopause, is commonly considered an aging disease present in both men and women. Individuals exhibiting osteoporosis are very prone to fractures, most commonly in the wrist, spine and hips. Death rates among men and women due to complications associated with osteoporosis are quite significant, numbering in the tens of thousands a year in North America. Experience has revealed no single measure of bone quality or quantity that is a reliable indicator of fracture risk. For example, microcracks from prior stresses increase risk but are not "visible" in most measurements. Nevertheless, it is widely accepted that the strength of bone (i.e., its resistance to fracture) is roughly proportional to the mass density of the bone mineral and this, in turn, is proportional to the calcium content.

New treatments and therapies have recently been, and are currently being, developed to treat osteoporosis. Two basic approaches to treatment are taken; one relates to intervening in order to reduce the amount of bone loss which accompanies aging, and the other involves replacing lost calcium or increasing calcium content. Early detection of bone mineral loss would be very advantageous, particularly if steps can be taken in the very early stages to slow down calcium depletion. The ability to measure, noninvasively and in situ, bone mineral content is crucial to early detection of osteoporosis and other related skeletal degenerative diseases.

There are several techniques available for measurement of bone mineral content. Computed tomography (CT) involves measurement of X-rays transmitted through the different parts of the anatomy detected by arrays of detectors whereupon cross-sectional images are constructed of internal structures of the body from transmitted X-ray data from which mineral loss data is obtained. Dual energy X-ray absorptometry (DXA) uses a dual energy approach in order to correct for tissue variations and to permit quantification of bone mass.

More specifically, U.S. Pat. No. 5,535,750 issued to Matsui et al. is directed to a method and device for monitoring development of osteoporosis using ultrasonic monitoring of a heel or a knee bone. The method involves measurement of velocity differences of acoustic signals transmitted through the subject bones.

U.S. Pat. No. 5,483,965 issued to Weiner et al. teaches insertion of the heel of a person into a water bath in an apparatus containing ultrasonic transducers to perform densitometry. Acoustic signals are transmitted through the user's foot and a receiver on the other side of the foot detects the signals and measures the transit time and attenuation of a selected frequency thereby obtaining a profile of the bone content.

U.S. Pat. No. 5,335,260 issued to Arnold is directed to a method of quantifying calcium, bone mass and bone mass density via X-ray radiography that involves use of a calibration phantom comprising a material to simulate human tissue. X-rays of sufficient energy and intensity are transmitted through the limb and a detector on the other side of the limb processes the transmitted X-ray data.

U.S. Pat. No. 5,204,888 issued to Tamegai et al. discloses a method for measurement of bone mineral content through irradiating an object with X-rays and measuring the transmitted X-ray intensity. The device uses an X-ray generator that produces X-rays over a continuous spectrum and a detector placed on the other side of the object being probed to measure transmitted X-ray intensities.

U.S. Pat. Nos. 4,510,450 and 4,635,643, both issued to Brown teach use of nuclear magnetic resonance for determining mineral content of bone. U.S. Pat. No. 4,510,450 claims a rotor device which acts as a holder for the assay during the test and U.S. Pat. No. 4,635,643 claims the actual method of probing for mineral content using $^{31}$P NMR.

U.S. Pat. No. 5,521,955 issued to Gohno et al. discloses an apparatus for bone density measurement and non-destructive inspection using a computed tomography (CT) scanner. The method requires scanning a calibration sample produced by mixing a water equivalent material (a material having the same X-ray transmission rate as that of water) with different ratios of a standard material equivalent to bone mineral mass (a material having the same X-ray transmission rate as that of bone mineral mass) and determining the bone density relative to the standard samples.

U.S. Pat. No. 4,829,549 issued to Vogel et al. is directed to a densitometer for predicting osteoporosis by measurement of bone mineral content by transmission of X-rays/gamma rays through the heel bone. A foot holder is provided with a radioactive source holder mounted in the foot holder along with a detector mounted in the foot holder opposite the source holder, U.S. Pat. No. 5,351,689 issued to MacKenzie teaches a method and apparatus for low dose estimates of bone minerals using gamma ray backscattering. The method disclosed in this patent relies upon measuring the backscattering from bones and comparing the intensities in two areas of the backscatter spectrum. One area, $A_1$, derives most of its intensity from Rayleigh scattering while the other area, $A_2$, combines the events from both Rayleigh and Compton scattering. The shape parameter, $W=A_1/A_2$, is approximately a linear function of bone mineral content because most of the Rayleigh scattering is due to calcium content of the bone mineral.

A drawback to many of the above-mentioned devices and procedures for measuring bone content is the need for very expensive, large and heavy equipment and in some cases high radiation doses. Such systems, for example the DXA and CT systems require a dedicated centralized location and require attendance by specialized technicians to oversee the scanning process. This results in availability being restricted to medical facilities that are financially well supported.

Therefore, it would be very advantageous to provide an in vivo, low dose, rapid and inexpensive method and device for monitoring bone mineral content that is portable and does not require sophisticated analysis techniques for interpreting the results. Such a device would readily lend itself to large scale use and may be used by any age group for monitoring bone development and would be very useful as a first tool in a program for early detection and prevention of osteoporosis as well as for monitoring the effectiveness of any dietary or pharmaceutical therapeutic program in respect of impact on bone mineral content.

SUMMARY OF THE INVENTION

It is an object of the present invention to provide a method and apparatus for estimating bone mineral content of certain trabecular bones.

It is also an object of the present invention to provide a method for monitoring osteoporosis using the X-ray albedo of the calcaneus.

The present invention provides a non-destructive, low dose, in-situ method of estimating bone mineral content by measuring the intensity of X-rays backscattered from certain trabecular bones.

In one aspect of the present invention there is provided a low dose in vivo method for estimating bone mineral content of certain trabecular bone. The method comprises immobilizing a person's anatomical part containing trabecular bone;

providing a source of X-rays wherein at least some of the X-rays emitted therefrom have an energy in a range so that absorption of the X-rays by calcium competes with scattering of the X-rays by calcium and other constituents making up the trabecular bone;

irradiating a target trabecular bone in the anatomical part with a low radiation dose from the X-ray source;

measuring an intensity of backscattered X-ray radiation from a person's anatomical part; and estimating a bone mineral concentration in a trabecular bone from the intensity of backscattered X-ray radiation.

In this aspect of the invention the step of irradiating a target trabecular bone may include irradiating the target trabecular bone with X-ray radiation from a radioactive $^{109}$Cd source or other suitable radioactive source or X-ray tube.

In another aspect of the invention there is provided an apparatus for low dose in vivo measurement of bone mineral content of trabecular bones, comprising:

a support frame and securing means for immobilizing a person's anatomical part containing a trabecular bone to the support frame;

a detector mounted on the support frame for detecting an intensity of X-rays;

an X-ray source positioned with respect to the detector so that a beam of X-rays is directed away from the detector into a person's immobilized anatomical part, the detector being positioned with respect to the X-ray source to measure an intensity of X-rays backscattered from the trabecular bone, wherein at least some of the X-rays in the beam have an energy in a range so that absorption of the X-rays by calcium competes with scattering of the X-rays by calcium and other constituents making up a trabecular bone; and a processor for calculating a bone mineral concentration of the trabecular bone from the intensity of backscattered X-rays.

In another aspect of the present invention there is provided a method for low dose monitoring calcium content of a person's calcaneus, comprising:

a) immobilizing a person's foot containing a calcaneus;

b) providing a source of X-rays wherein at least some of the X-rays emitted therefrom have an energy in a range so that absorption of the X-rays by calcium competes with scattering of the X-rays by calcium and other constituents making up the calcaneus, and irradiating the calcaneus with a low radiation dose from the source of X-rays;

c) measuring an intensity of X-rays backscattered from the person's foot;

d) estimating a calcium concentration in the calcaneus from the intensity of backscattered X-rays; and e) repeating steps a) to d) periodically and monitoring any changes in X-ray albedo of the calcaneus to determine if the calcium concentration is changing over time.

BRIEF DESCRIPTION OF THE DRAWINGS

The method and device for estimating calcium content of trabecular bones will now be described, by way of example only, reference being had to the following drawings.

DETAILED DESCRIPTION OF THE INVENTION

The present invention provides a method and device for an in situ, low dose estimation of bone mineral content of certain trabecular bones by measuring the total intensity of X-rays backscattered from the trabecular bone. Periodic measurements of the person using the present method and device permits one to monitor the development of osteoporosis based on changes in the X-ray albedo of the trabecular bone resulting from varying concentrations of calcium phosphate over time.

Figure 1:
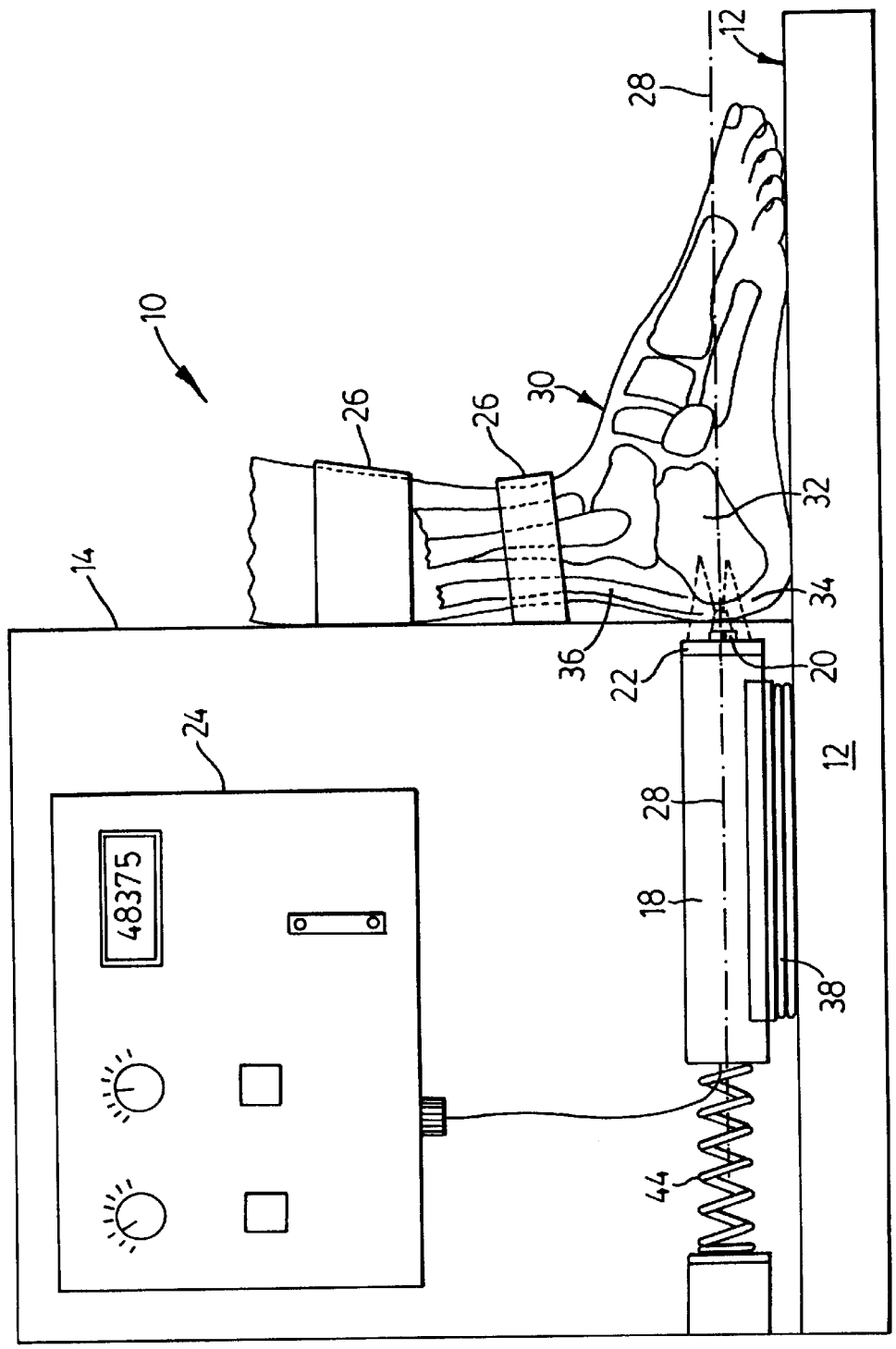
FIG. 1 shows a vertical view of the device for estimating calcium in a person's calcaneus constructed in accordance with the present invention.

Referring to FIG. 1 an apparatus for estimating calcium content of trabecular bones such as the calcaneus (heel bone) is shown generally at 10. Apparatus 10 includes a platform 12 which provides a foot and leg support for a user's foot 30. A housing 14 encloses a radioactive source/detector assembly 18 mounted therein. The source/detector assembly 18 comprises an axially symmetric heavy-metal radioactive source holder (collimator) 20 containing a radioactive source mounted on the cylindrical axis 28 of a cylindrically symmetric radiation detector 22, for example, a NaI(Tl) scintillation counter and photomultiplier. Source/detector assembly 18 is connected to a control circuit 24 which while shown mounted in housing 14 may be located away from the housing. Control circuit 24 is connected to detector 22 and includes timing circuits and processors to process the data from the detector. Restraining straps 26 are used to hold the user's foot 30 immobile on apparatus 10.

Figure 2:
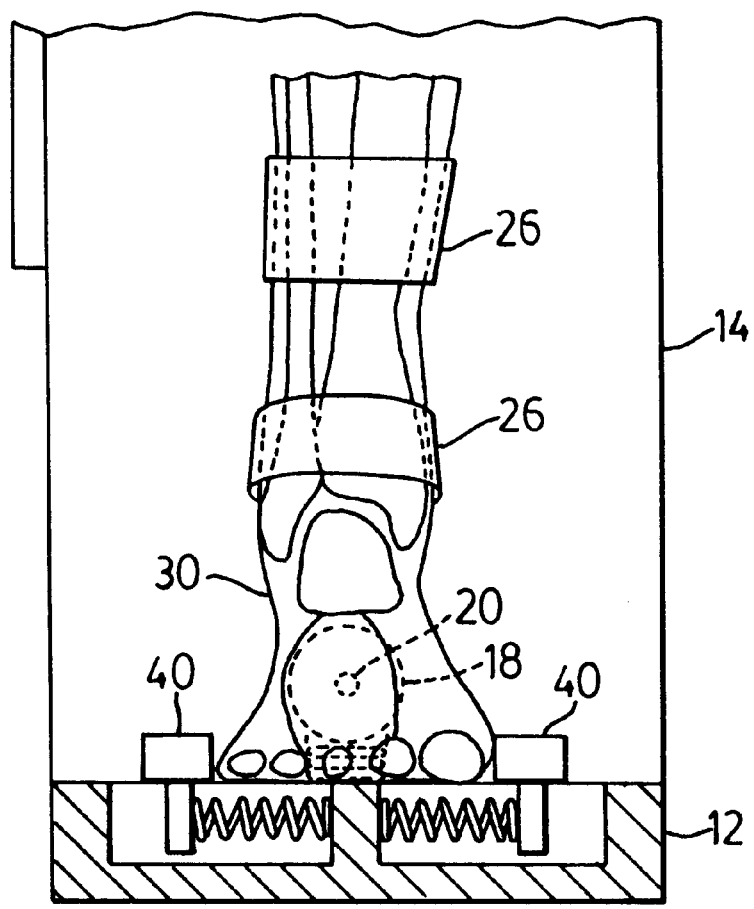
FIG. 2 is a view along line 28 of FIG. 1.

Measuring the calcium concentration of the calcaneus is preferred for reasons to be discussed hereinafter. The source holder/detector assembly 18 is mounted in housing 14 so that when a user's foot 30 is immobilized on apparatus 10 the source-holder 20, which is spring-loaded using a spring 44 to compress the soft tissue in region 34, is held firmly against the centre of the rear of the patient's heel so the X-rays penetrate through the soft tissue 36. An alignment mechanism 38 allows assembly 18 to be raised and lowered and moved side-to-side and oriented in the vertical plane to allow adjustment to differently sized feet. Referring to FIG. 2, two alignment beams 40 are disposed on each side of the person's foot on platform 12 and spring biased inwardly so that when a user places his or her foot on the platform it is held in alignment by beams 40.

The apparatus exploits the cylindrical symmetry of the source containing collimator 20 and detector 22 and uses shadowing or geometric hindrance by the heavy-metal collimator to prevent both primary X-rays from the source and X-rays backscattered from the soft tissue under the skin covering the calcaneus in region 34 (FIG. 1) from reaching detector 22. The shape of the source holder 20 can be designed to give the desired amount of collimation of the X-ray beam. The beam of X-rays emanating from collimator 20 is backscattered from the constituents making up the calcaneus, as can be seen from the broken ray lines in FIG. 1. The backscattered X-rays can be counted very efficiently by detector 22, provided that these X-rays reach the detector without being absorbed.

The preferred radioactive source is $^{109}$Cd that emits the K X-rays of silver (22 to 25 Kev) but other suitable radioactive sources or an X-ray tube may be used. The collimator 20 directs the cone of primary X-rays along the axis 28 of the detector 22 but in the opposite direction away from the detector. The method relies upon measuring the intensity of X-rays backscattered from the various components making up the calcaneus (heel bone) 32 and relating this intensity to the concentration of calcium present. All of the tissues of the human body are very weak absorbers of 20 keV X-rays with the sole exception of bone. Even the bone is a weak absorber except for that part of the bone that is in the form of a mineral called apatite. Apatite comprises mainly calcium phosphate of which calcium is the main X-ray absorber and therefore to a good approximation the observed counting rate gives a measure of the calcium content of the heel; the more calcium, the lower the counting rate and the relationship between counting rate and calcium content has been observed to be smoothly varying and approximately linear.

X-rays are backscattered primarily via Compton scattering (although Rayleigh scattering also contributes to scattering) and are detected by the scintillation detector. The end portion of the detector/source assembly 18 containing the collimator 20 is held firmly against the lateral centre of the rear of the person's heel so that the X-rays penetrate through the compressed soft tissue region 34 containing the Achilles tendon 36 (FIG. 1 )and in a direction more or less parallel to the sole of the foot 30. This means that the X-rays penetrate into the calcaneus after penetration of about 5 mm of tendon and other soft tissues that cover the calcaneus in region 34. Most of the X-rays will collide with electrons in the chemical constituents of the calcaneus in the process of Compton scattering. In this process, the X-rays lose some of their energy, the loss depending on the angle at which they are scattered. Those X-rays that are scattered back toward the detector 22 have a distribution of energies centred approximately around 20 keV.

For purposes of monitoring osteoporosis in humans, the calcaneus is the preferred bone to monitor because it has the highest percentage of spongy or trabecular bone in the human body so that this bone is most sensitive to osteoporosis being the best predictor of fracture risk. In addition to the mineral constituent of calcium phosphate, the calcaneus also comprises collagen, a biological polymer, and bone marrow which is primarily fat. Both collagen and bone marrow are normally classified as soft tissue. The calcaneus is more simple in external shape and internal structure compared to say, a vertebra. The specific arrangement of the source-holder bearing against the back of the heel is highly preferred because it exploits the size and shape of the calcaneus when accessed by X-rays in the above-noted direction. This location is also most accessible with a small amount of soft tissue between the calcaneus and the portion of the skin on the heel against which the source holder 20 (FIG. 1) is engaged. For monitoring the calcium content of the heel bone there is required an X-ray energy that is capable of penetrating about 1 cm into a healthy calcaneus. This will ensure a much deeper penetration into an osteoporotic calcaneus because of the relative lack of calcium and hence decreased photoelectric absorption. The X-ray energy must be low enough to ensure a strong contrast in the absorption of both the primary and scattered X-rays because of the presence of calcium. X-rays in the range of 15 to 30 keV can be used but a $^{109}$Cd source is preferred since it emits X-rays in the range of 22 to 25 keV.

As mentioned above, it is predominantly Compton scattering that causes scattered X-rays to be directed back to the detector 22. The greater the density of the material, the more Compton scattering occurs and so normally it would be anticipated that an increase of bone mineral density would lead to an increase in backscatter intensity. However, the opposite occurs in the present invention because the energy of the X-rays has been chosen such that it is primarily the chance of absorption by calcium (rather than the chance of scattering) that determines the backscattered X-ray intensity.

It is noted that the contrast is not due to the difference of absorption and scattering by the calcium alone. Even in a non-osteoporotic calcaneus, most of the scattering is done by the other components making up the calcaneus rather than the calcium. So the objective is to achieve a situation in which absorption by calcium competes on more or less equal terms with scattering by the combination of these other components and calcium. This competition between scattering and absorption is quantified by using the concept of albedo, a concept in common use in meteorology; the whiter an object, the lower the absorption and the higher the albedo. Therefore, by making periodic measurements of the calcium content of the person's calcaneus the present invention can be used to monitor the development of osteoporosis based on changes in the X-ray albedo of the calcaneus resulting from varying concentrations of calcium phosphate over time.

In the X-ray albedo measurement, the main effect is that the volume of the target that is "sampled" by the X-rays is determined by the total absorption. If the target has a very low absorption (such as a very osteoporotic heel) the counts are received from a large approximately conical shaped volume of the heel. As calcium content increases (progressively more healthy calcanei) the sample volume keeps its roughly conical shape but the volume decreases because backscattered photons are absorbed before they can reach the detector. The sampled volume is not quite that of a solid cone because shielding (or shadowing) by the source holder results in a "dead-zone" near the apex of the cone. This dead zone is axially symmetric and has a re-entrant shape similar in shape to the bottom of a champagne bottle.

More specifically, with respect to shadowing, the source holder 20 must be designed to provide sufficient shielding to prevent the primary photons from going directly to the detector in numbers that would mask the signals originating from the backscatter in the target. If the source holder has the shape of a circular cylinder its minimum diameter has to be about 6 mm. When such a source holder is pressed against a solid, low-Z target it is clear that the source holder will also shield the detector from secondary photons produced by scattering close to the source holder and along or close to its axis. In other words there is a "dead zone" of a shape similar to the cavity in the bottom of a champagne bottle. The source holder shades the detector from single scattering events occurring in this "dead zone".

The dead zone is not large for a holder of the minimum 6 mm diameter and we find that the peak sensitivity occurs at depths of only about 5 mm in the target. If such a system were used to measure backscatter from a human heel about half the counts would result from scattering in the soft tissue covering the calcaneus. There would be very little sensitivity to the calcium content of the calcaneus because most of the photons would not have reached it either as primaries or secondaries.

"Shadowing" is a term the inventor uses when consciously designing a source holder of more than the minimum diameter with the express purpose of enlarging the "dead zone", moving the response peak to a greater depth and forcing the detected photons, both primaries and secondaries to travel a greater minimum distance before reaching the detector. If the target contains an efficient photon absorber (such as the calcium in the calcaneus) then the chance of absorption is increased. The greater the distance travelled by the photons in the absorbing medium with linear absorption coefficient, $\mu$, the greater is the reduction in intensity by a factor of $e^{-\mu x}$.

The inventor has found that the peak of the sensitivity can be displaced to a depth of about 12 mm by using a source holder with a diameter of about 19 mm. The system then shows a much higher sensitivity to the calcium content of homogeneous phantoms. Optimum dimensions of the source holder are not sharply defined because there is a compromise between the beneficial effects of increasing the path length for single collisions and the deleterious effects of increasing the fraction of double scattering events, some of which would occur in soft tissues external to the calcaneus.

Since no image of the bones is formed, the calcaneus is treated as if it were a homogeneous structure and calibration standards are produced by constructing homogenous Vaseline (petroleum jelly) phantoms containing known amounts of calcium phosphate ($CaHPO_4$). Finely powdered $CaHPO_4$ is sufficiently similar in density to petroleum jelly that it can form a mechanically stable mixture over a very long period at room temperature. The viscosity of petroleum jelly is sufficient to keep the phosphate in suspension for years without detectable segregation. The phantoms were constructed by mixing appropriate masses of petroleum jelly and $CaHPO_4$ in a mixing dish, stirring to achieve homogeneity and then putting the mixture in standard 250 ml NALGENE (high density polyethylene) bottles and removing air bubbles Nalgene bottles of 60 mm diameter were wrapped with a thin layer of lead (~0.5 mm thick) so that the total X-ray backscatter would not be influenced by any materials surrounding the bottles.

These nalgene phantoms are similar in size to a human heel and are designed to fit into the foot holder. Phantoms containing between 0 and 50% $CaHPO_4$ by mass were constructed and used to calibrate the measuring system.

The level of desired contrast is determined in part by the design of the collimator. To obtain high contrast (i.e. sensitivity to changes in calcium content), a large diameter for the source holder is preferred and, to achieve a reasonable counting rate, a strong source is also required. If low contrast is acceptable, then a source holder with a smaller diameter will suffice along with a weaker radioactive source. As the radioactive source strength decreases the precision decreases (roughly as the square root of the inverse source strength). Use of detectors with high counting efficiency allows weaker intensity sources to be used. The operative upper limit of the source strength is determined by the counting rate the detection system can tolerate. Depending on contrast requirements and the counting electronics, radioactive sources with source strengths in the range from about 10 microcuries to about 10 millicuries may be used. To ensure a low dose during the measurement of the calcium content of the person's calcaneus, measurements using higher source strengths are carried out for shorter periods of time compared to measurements carried out with lower source strengths.

In view of the fact that the strength of a bone (i.e., its resistance to fracture) is proportional to the mass density of the bone mineral and this, in turn, is proportional to the calcium content, the method disclosed herein for measurement of the intensity of the backscattered X-rays is a good indicator of the weakness of the bone, with the weaker bones giving higher backscattered X-ray intensities.

The present invention measures an X-ray backscattering intensity that decreases linearly with the mean volumetric density of bone mineral and hence the results can be expressed in units of grams/cubic centimetre. In contrast the DXA method provides an areal mineral density in units of grams/square centimeter. This is performed by determining the mineral content with a measured surface area of bone. Errors can occur due to variations in the depth (or thickness) of the bone measured.

In the present method the constant that relates backscattered intensity to the mean bone mineral density is very insensitive to internal structure of the calcaneus because the sampled volume is several cubic centimeters. A simple subsidiary measurement corrects for the thickness of soft tissues covering the calcaneus.

Therefore, while the present invention has been described and illustrated with respect to the preferred embodiments for estimating mineral content of trabecular bones, it will be appreciated that numerous variations of these embodiments may be made depending on the application without departing from the scope of the invention as described herein.

Therefore what is claimed is:

1. A low-dose in vivo method for measuring bone mineral concentration in trabecular bone, comprising:
    immobilizing a person's anatomical part containing trabecular bone;
    providing a source of X-rays wherein at least some of said X-rays emitted therefrom have an energy in a range so that absorption of said X-rays by calcium competes with scattering of said X-rays by calcium and other constituents making up trabecular bone;
    irradiating a target trabecular bone in an anatomical part with a low radiation dose from said X-ray source;
    measuring an intensity of backscattered X-ray radiation from a person's anatomical part; and
    estimating a bone mineral concentration in a trabecular bone from the intensity of backscattered X-ray radiation.

2. The method for estimating bone mineral content according to claim 1 wherein the step of irradiating a target trabecular bone includes at least irradiating said target trabecular bone with X-ray radiation from a radioactive [109]Cd source.

3. The method for estimating bone mineral content according to claim 2 wherein the steps of immobilizing a person's anatomical part and irradiating a target trabecular bone includes at least immobilizing a person's foot with a collimator containing said radioactive [109]Cd bearing against the back of the person's heel whereby the X-rays are directed toward the calcaneus along an axis of the person's foot substantially parallel to the sole of the foot.

4. The method for estimating bone mineral content according to claim 3 wherein the step of estimating mineral content of the trabecular bone from the intensity of backscattered X-rays includes at least comparing the intensity of the backscattered X-rays from the calcaneus to an intensity of X-ray radiation backscattered from a set of reference standards using the same radioactive $^{109}$Cd source, and wherein each reference standard contains a preselected amount of calcium phosphate.

5. The method for estimating bone mineral content according to claim 3 wherein the step of providing a source of X-rays includes providing a source having a cylindrical shape whereby X-rays produced by said source exit said source holder in a conical shaped beam.

6. The method for estimating bone mineral content according to claim 2 wherein the radioactive $^{109}$Cd source has a source strength in the range of from about 10 microcuries to about 10 millicuries.

7. An apparatus for in vivo measurement of bone mineral content of trabecular bones, comprising:
 a support frame and securing means for immobilizing a person's anatomical part containing a trabecular bone to said support frame;
 a detector mounted on said support frame for detecting an intensity of X-rays;
 an X-ray source positioned with respect to said detector so that a beam of X-rays is directed away from said detector into a person's immobilized anatomical part, the detector being positioned with respect to said X-ray source to measure an intensity of X-rays backscattered from said trabecular bone, wherein at least some of said X-rays in said beam have an energy in a range so that absorption of the X-rays by calcium competes with scattering of said X-rays by calcium and other constituents making up a trabecular bone; and
 a processor for calculating a bone mineral concentration in the trabecular bone from said intensity of backscattered X-rays.

8. The apparatus according to claim 7 including a heavy-metal source holder, said X-ray source being located in said source holder, said source holder being positioned with respect to said detector so that said source holder and detector have a common axis of symmetry and a collimated X-ray beam emerges from a front end of said source holder away from said detector.

9. The apparatus according to claim 8 wherein said support frame includes at least a support for supporting a person's foot containing a calcaneus, the source holder being mounted on said frame so that when a person's foot is immobilized on said foot support the X-ray source is located behind a person's heel so that the X-rays are directed toward the calcaneus along an axis of a person's foot substantially parallel to the sole of the foot.

10. The apparatus according to claim 7 wherein said X-ray source is a radioactive $^{109}$Cd source.

11. The apparatus according to claim 8 wherein the detector is a cylindrically symmetric detector having a cylindrical axis, and wherein the heavy-metal source holder is a cylindrically symmetric source holder mounted along the cylindrical axis on a front portion of said detector, and wherein said detector is a NaI(Tl) scintillation counter and photomultiplier combination.

12. The apparatus according to claim 8 including at least a positioning means for positioning said source holder and detector with respect to said anatomical part.

13. The apparatus according to claim 9 including at least a positioning means for positioning said source holder and detector with respect to a person's foot immobilized in said support.

14. The apparatus according to claim 10 wherein the radioactive $^{109}$Cd source has a strength in the range of from about 10 microcuries to about 10 millicuries.

15. A method for low-dose monitoring calcium content of a person's calcaneus, comprising:
 a) immobilizing a person's foot containing a calcaneus;
 b) providing a source of X-rays wherein at least some of said X-rays emitted therefrom have an energy in a range so that absorption of said X-rays by calcium competes with scattering of said X-rays by calcium and other constituents making up said calcaneus, and irradiating said calcaneus with a low radiation dose from said source of X-rays;
 c) measuring an intensity of X-rays backscattered from the person's foot;
 d) estimating a calcium concentration in said calcaneus from the intensity of backscattered X-rays; and
 e) repeating steps a) to d) periodically and monitoring any changes in X-ray albedo of the calcaneus to determine if the concentration of calcium is changing over time.

16. The method according to claim 15 wherein the source of X-rays is a radioactive $^{109}$Cd source.

17. The apparatus according to claim 8 wherein the source holder substantially blocks primary X-rays from the X-ray source, and wherein said source holder has an effective diameter to substantially block secondary photons scattered in a volume adjacent to said front end of the source holder from hitting said detector.

18. The method according to claim 1 wherein the X-ray source is contained in a source holder, said source holder being positioned with respect to said detector so that said source holder and detector have a common axis of symmetry and a collimated X-ray beam emerges from a front end of said source holder away from said detector, and wherein said source holder is a heavy metal source holder which substantially blocks primary X-rays from the X-ray source hitting said detector.

19. The method according to claim 18 wherein said source holder has an effective diameter to substantially block secondary photons scattered in a volume adjacent to said front end of the source holder from hitting said detector.

20. The method according to claim 1 wherein said X-ray source emits X-rays having energies in a range from about 15 to about 30 keV.

21. The apparatus according to claim 7 wherein said X-ray source emits X-rays having energies in a range from about 15 to about 30 keV.

22. The method according to claim 15 wherein said X-ray source emits X-rays having energies in a range from about 15 to about 30 keV.

* * * * *